(12) United States Patent
Desarzens et al.

(10) Patent No.: US 8,182,486 B2
(45) Date of Patent: May 22, 2012

(54) GUIDED REAMER SYSTEM FOR RESHAPING BONE

(75) Inventors: Yves Desarzens, Corgemont (CH); Andre Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 727 days.

(21) Appl. No.: 11/932,988

(22) Filed: Oct. 31, 2007

(65) Prior Publication Data

US 2008/0108999 A1 May 8, 2008

Related U.S. Application Data

(63) Continuation of application No. 11/117,740, filed on Apr. 29, 2005, now Pat. No. 8,057,477.

(51) Int. Cl.
*A61B 17/00* (2006.01)

(52) U.S. Cl. .......................................................... 606/80

(58) Field of Classification Search .......... 606/1, 79–81, 606/86 R
See application file for complete search history.

(56) References Cited

U.S. PATENT DOCUMENTS

| | | | | |
|---|---|---|---|---|
| 2,804,865 A * | 9/1957 | Hillber | .................. | 123/185.1 |
| 3,605,527 A * | 9/1971 | Gambale | ................. | 76/115 |
| 5,180,384 A * | 1/1993 | Mikhail | .................. | 606/80 |
| 5,484,437 A * | 1/1996 | Michelson | .................. | 606/86 A |
| 5,514,141 A * | 5/1996 | Prizzi, Jr. | .................. | 606/80 |
| 5,928,238 A * | 7/1999 | Scarborough et al. | .......... | 606/79 |
| 6,277,121 B1* | 8/2001 | Burkinshaw et al. | .......... | 606/80 |
| 6,332,886 B1* | 12/2001 | Green et al. | .................. | 606/80 |
| 6,475,221 B1* | 11/2002 | White et al. | .................. | 606/80 |
| 6,730,094 B2* | 5/2004 | Salyer et al. | .................. | 606/80 |
| 7,229,078 B2* | 6/2007 | Lechot | .................. | 279/93 |
| 2003/0135219 A1* | 7/2003 | Salyer et al. | .................. | 606/81 |
| 2004/0030343 A1* | 2/2004 | Kurc | .................. | 606/80 |
| 2004/0193168 A1* | 9/2004 | Long et al. | .................. | 606/80 |

* cited by examiner

*Primary Examiner* — Thomas C. Barrett
*Assistant Examiner* — Michael Araj
(74) *Attorney, Agent, or Firm* — Michael F. Scalise

(57) ABSTRACT

A reamer system is provided which includes a cannulated reamer handle, and a corresponding cannulated reamer, which, when assembled and operated over a drill pin secured in a manner axially aligned with the stem of the femoral joint, enables the accurate and controlled reshaping of the femoral joint. The reamer is made up of a cutting form and a central guide, in which the guide is supported at the center of the cutting form by a bar structure. The bar structure includes portions which connect to and extend radially between the central guide and a peripheral edge of the cutting form. Optionally, the central guide includes a surface offset from a plane of the bar structure to a degree which enables that surface to contact an associated surface referenced to the bone, in order to prevent the cutting form from plunging so far over the bone as to potentially damage the femoral stem. This offset surface is preferably polished to reduce friction during relative rotational movement between this surface and the surface referenced to the bone. The offset surface is an axially perpendicular surface of a boss through which the drill pin is guided.

27 Claims, 7 Drawing Sheets

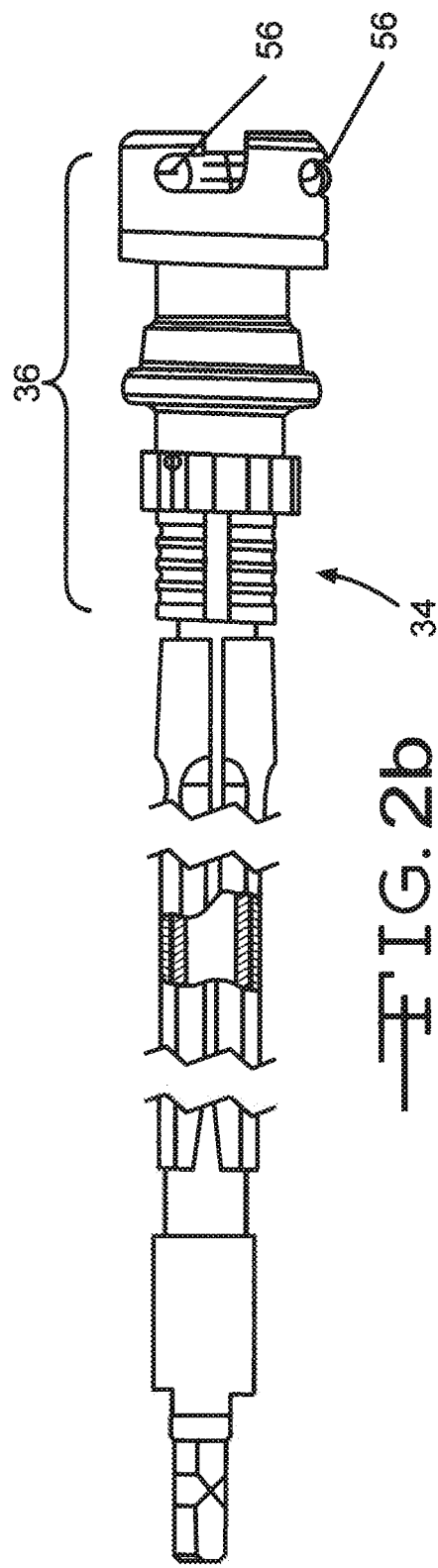
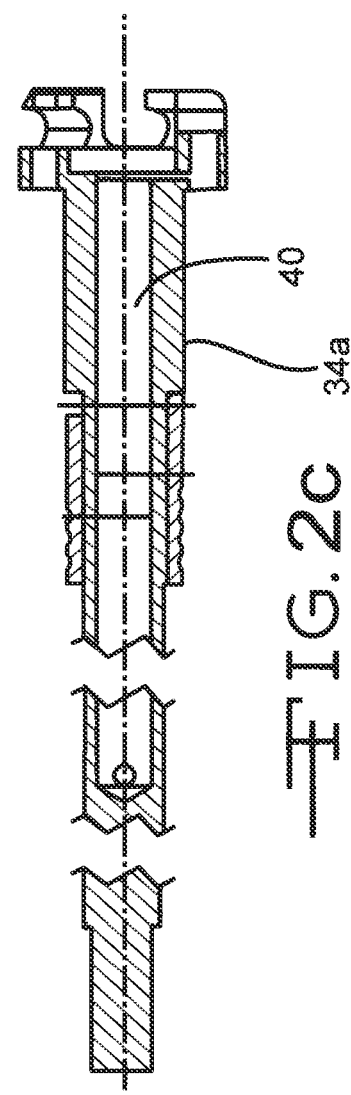
FIG. 2b
FIG. 2c

GUIDED REAMER SYSTEM FOR RESHAPING BONE

CROSS REFERENCE TO RELATED APPLICATION

This application is a continuation of U.S. application Ser. No. 11/117,740 of the same name, filed Apr. 29, 2005, now U.S. Pat. No. 8,057,477 the contents of which are incorporated herein by reference thereto.

BACKGROUND OF THE INVENTION

The invention relates to a bone shaping system made up of an instrument holder and a surgical instrument for attachment to the holder. The holder includes a shank equipped with a head designed to receive an instrument, and an annular locking component mounted so as to slide about the shank, under the head, equipped with locking means which cooperate with the head so as to lock the instrument on the head, and pushed against the head by a helical spring.

One such system is described in European Patent 0782840, the content of which is incorporated herein by reference thereto, and includes a shaft (10), equipped at one end with a cutting head holder (12) which has a bayonet joint and lock. A hemispherical or conical rotary cutting head (1) has inner radial rods (4) to engage with the bayonet joint. The cutting head contains an axial guide tube (5) between the inner ends of the radial rods and a central aperture (3) to receive a twist drill (9) which makes a hole in the middle of the recess formed by the cutting head. The lower end of the guide tube has one or more notches to receive corresponding studs on the twist drill so they rotate together. The holder (12) has a projection to block the drill in the guide tube. Additionally, the end of the guide tube, which adjoins the centre of the cutting head, has at least two projecting cutting teeth. Where a central hole in the recess is not required, a shorter twist drill is employed. However, while useful for controlling the cutting of the acetabulum, this system does not foresee a sliding fit between the reamer and the twist drill but rather one in which the two rotate together as a unit. Further, it is not contemplated that the drill be affixed to the bone and subsequently be used for guidance.

Other systems provide for reshaping of the bone, but the tool itself generally obstructs the view of the femoral lobe during cutting.

Therefore, there is a needed for cutters capable of cutting and shaping the femoral joint in preparation for the reception of a prosthetic cap. Such an application presents other challenges in guidance and control, particularly that of ensuring that the stem of the femoral joint is not damaged in the process.

What is needed therefore is a system which enables controlled cutting and reshaping of the femoral joint in preparation for the reception of a femoral cap prosthesis. What is needed is a system which does not completely obstruct the view of the femoral lobe when the reamer is placed over the lobe, ready for cutting or process thereof. Further, what is needed is a system that controls heat by moving any points of heat generation from the reamer to the holder, and thus away from the operative site.

SUMMARY OF THE INVENTION

A reamer system is provided which includes a cannulated reamer handle, and a corresponding cannulated reamer, which, when assembled and operated over a drill pin secured in a manner axially aligned with the stem of the femoral joint, enables the accurate and controlled reshaping of the femoral joint. The reamer is made up of a cutting form and a central guide, in which the guide is supported at the center of the cutting form by a bar structure. The bar structure includes portions which connect to and extend radially between the central guide and a peripheral edge of the cutting form. Optionally, the central guide includes a surface offset from a plane of the bar structure to a degree which enables that surface to contact an associated surface referenced to the bone, in order to prevent the cutting form from plunging so far over the bone as to potentially damage the femoral stem. This offset surface is preferably polished to reduce friction during relative rotational movement between this surface and the surface referenced to the bone. The offset surface is an axially perpendicular surface of a boss through which the drill pin is guided.

In a feature, the system provides a guidance surface in the holder and not primarily in the reamer, thus enabling moving a region of heat generation away from the cutting site, into the handle.

BRIEF DESCRIPTION OF THE DRAWINGS

FIG. 2b is a side view of the reamer holder of the system of the invention.

FIG. 2c is a side view of the shaft 34a of the holder of the system of the invention.

DETAILED DESCRIPTION OF THE PREFERRED EMBODIMENT(S)

Figure 1:
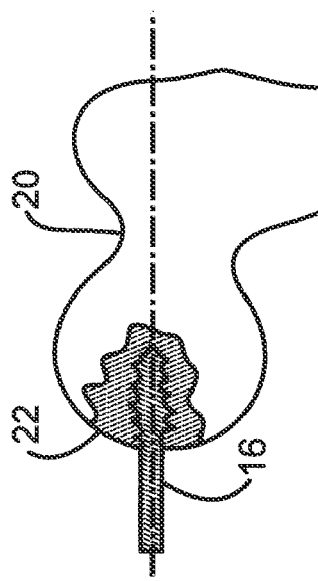
FIG. 1 is a schematic view of a femoral joint into which a bone pin is inserted.
Figure 2A:
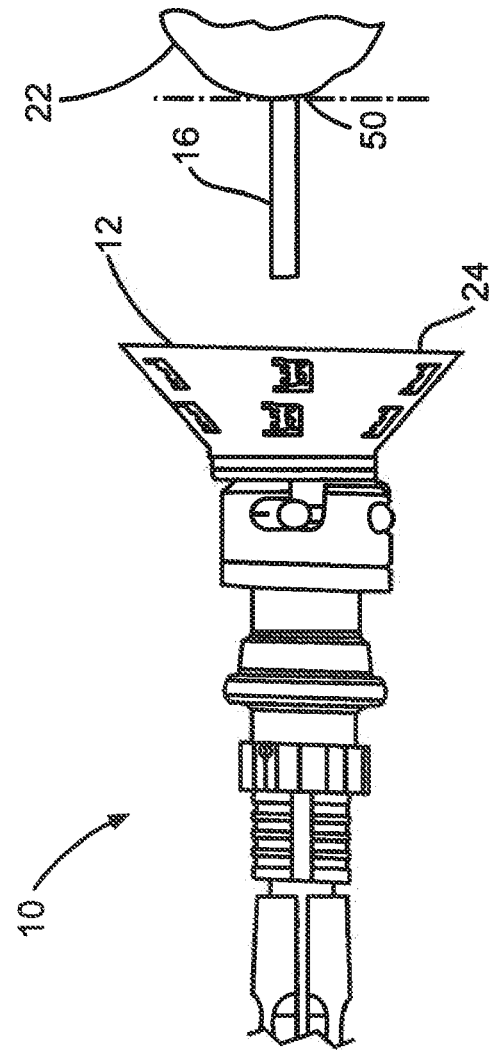
FIG. 2a is a side view of the system of the invention ready to be received at the operative site.
Figure 3A:
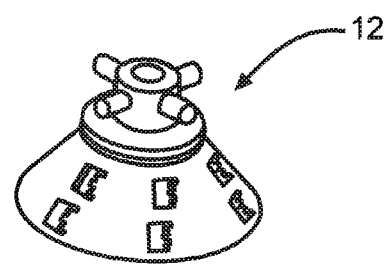
FIG. 3a is a perspective view of a reamer of the system of the invention.
Figure 3B:
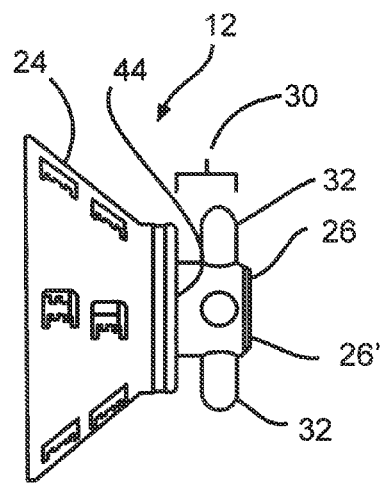
FIG. 3b is a side view of a reamer of the system of the invention.
Figure 3C:
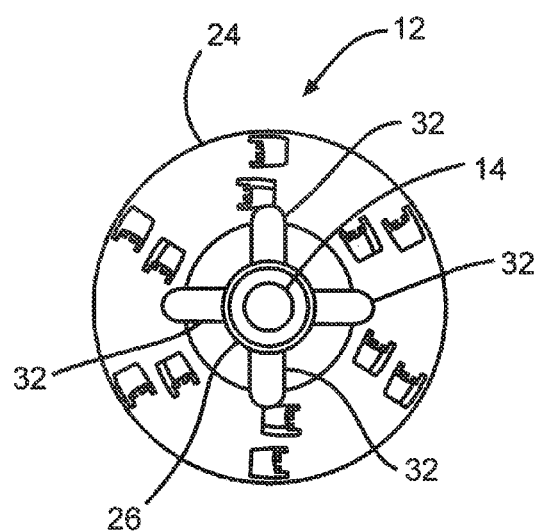
FIG. 3c is a top view of a reamer of the system of the invention.
Figure 4A:
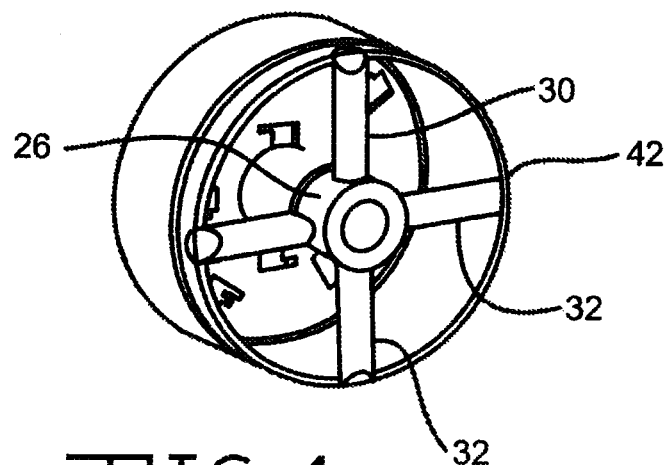
FIG. 4a is a perspective view of an alternate reamer of the system of the invention.
Figure 4B:
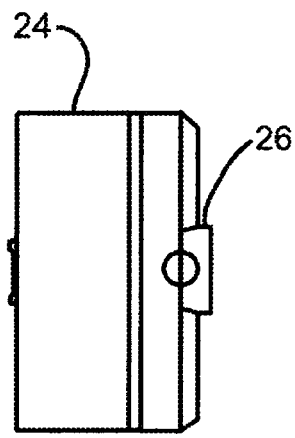
FIG. 4b is a side view of the alternate reamer of the system of the invention.
Figure 4C:
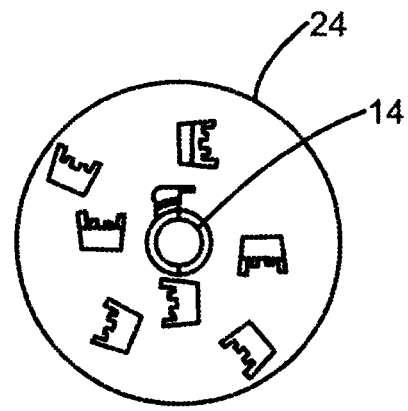
FIG. 4c is a top view of the alternate reamer of the system of the invention.

Referring now to FIG. 1, instead of a total hip replacement, which removes the organic stem 20 of a femoral joint 22 replacing it with an artificial one, processes exist that attempt to preserve the natural joint. One such procedure places a hard, external cap (not shown, but having an eternal spherical form which mates with a socket on its external side and over a resurfaced femoral joint via its internal surfaces). The cap is often made of metal and has precise interface dimensions which must be created on the bone in order for the cap to properly fit over the joint and to properly function in its corresponding prosthetic socket. A drill pin 16 is affixed to the joint 22, axially to the stem 20, in order to prevent damage to the stem, and to guide the cutting tool to precisely shape the joint.

Referring now to FIGS. 2a-2c and 3a-3c, the system 10 of the invention includes a cannulated reamer 12 and a cannulated reamer handle 34. The cannulated reamer 12 has a central cannulation 14 adapted to receive a drill pin 16 secured in a manner axially aligned with the stem 20 of the femoral joint 22. The reamer 12 has a profile cutting form 24 and a central axial guide 26. The guide 26 is supported at a center of the cutting form 24 by a bar structure 30. The bar structure 30 has portions 32 which connect to and extend radially from the central guide 26 and which non-rotatably connect to the cutting form 24.

The cannulated reamer handle 34 has a bayonet locking device 36 capable of locking the handle 34 to the cannulated reamer 12 and a corresponding central cannulation 40, permitting the drill pin 16 to pass therethrough. The bayonet locking mechanism 36 includes recesses 56 which catch portions of the bar structure 30.

The bar structure 30 is made up of a hollow post 26' attached to an apex 44 of the cutting form 24. The post has bars 32 attached thereto which are axially spaced apart and extend radially out from the post.

Referring in particular to the embodiments shown in FIGS. 4a-9, some of the portions 32 of the bar structure 30 extend and connect between the central guide 26 and a peripheral edge 42 of the cutting form 24.

Figure 5A:
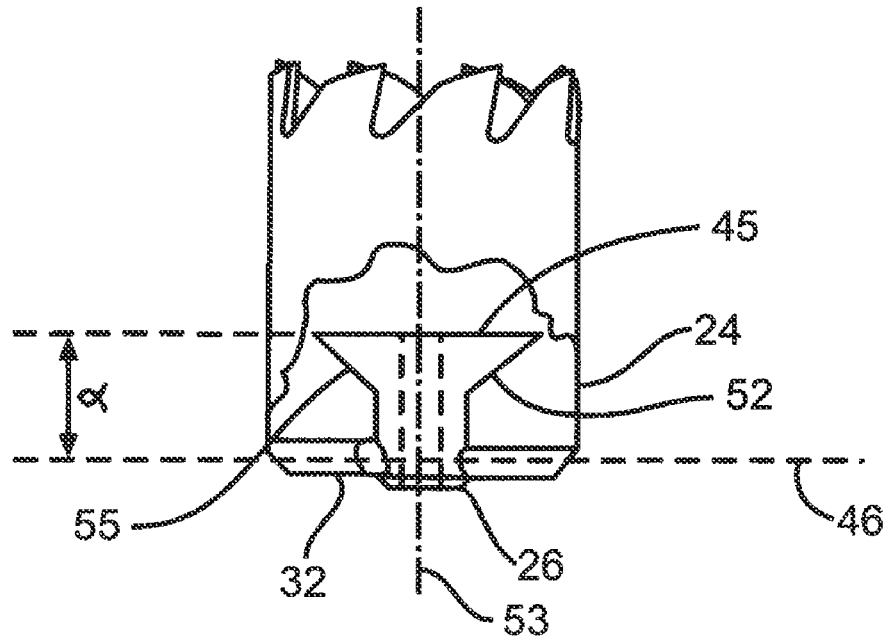
FIG. 5a is a partial cutaway, side view of a second alternate reamer of the system of the invention.
Figure 5B:
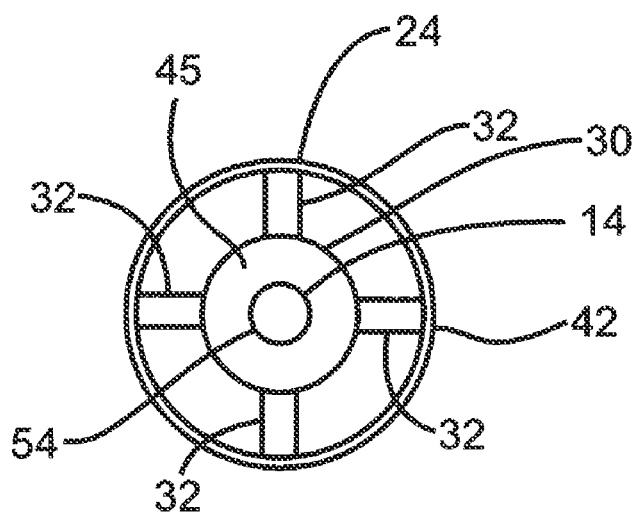
FIG. 5b is a top view of the second alternate reamer of the system of the invention.

Referring now to FIG. 5a, the central guide 26 includes a surface 44 offset from a plane 46 of the bar structure 30 at a distance d which enables that surface 45 to contact an associated surface 50 referenced to the bone 22, in order to prevent the cutting form 24 from plunging so far over the bone as to potentially damage the femoral stem 20. The offset surface 45 is preferably polished to reduce friction during relative rotational movement between this surface 45 and the surface 50 referenced to the bone 22. The offset surface 45 is an axially perpendicular surface of a boss 52 optionally possessing a flange 55 through which the drill pin 16 is guided via the axial hole 54 therethrough. The longitudinal axis of the cutting form 24 is indicated with numerical designation 53.

In a preferred embodiment, the reamer handle 34 has a central cannulation 40 which is polished or otherwise made to closely fit over the drill pin 16, so as to provide substantially all the guidance thereof. Thus, heat which is generated is moved in the reamer handle away from the operative site and thus less likely to cause damage to tissue or bone.

Figure 6:
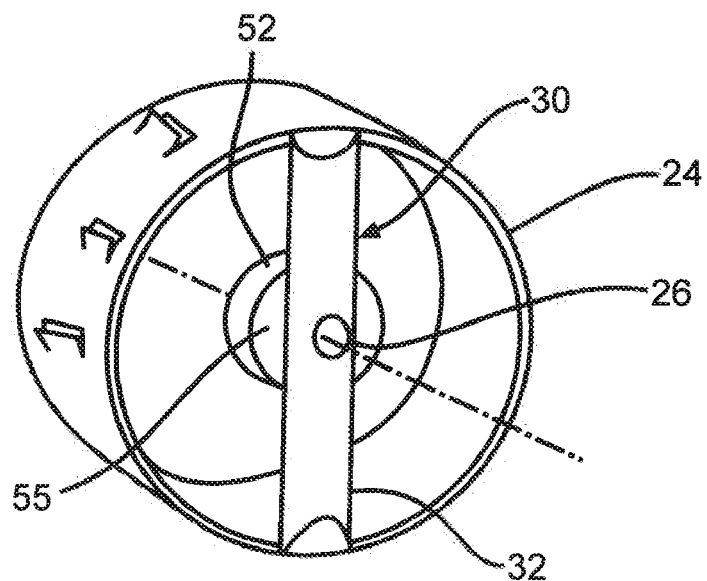
FIG. 6 is a perspective view of a third alternate reamer of the system of the invention.

Referring now to FIG. 6, the bar structure 30 is made up of a single bar 32, traversing a center of the cutting form 24. The central axial guide 26 is an axial hole 54 in the bar 32.

Figure 7:
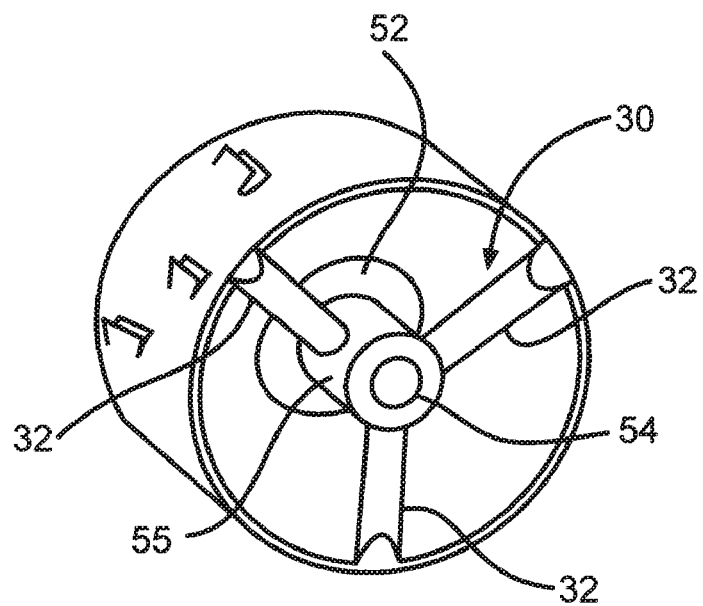
FIG. 7 is a perspective view of a fourth alternate reamer of the system of the invention.

Referring now to FIG. 7, the bar structure 30 is made up of three bars 32 connected to the central axial guide 26.

Figure 8:
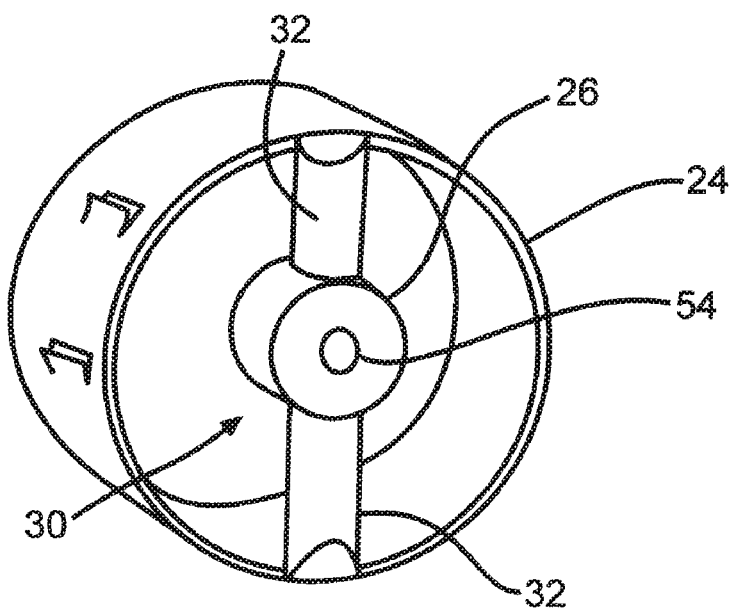
FIG. 8 is a perspective view of a fifth alternate reamer of the system of the invention.

Referring now to FIG. 8, the bar structure 30 is made up of at least two bars 32 traversing a center of the cutting form 24 and connected to the central axial guide 26 which has an axial hole 54 for receiving a drill pin 16.

Referring now to FIGS. 4a-4c, and 5a and 5b, the bar structure 30 is made up of four bars 32 connected to the central axial guide 26.

Figure 9:
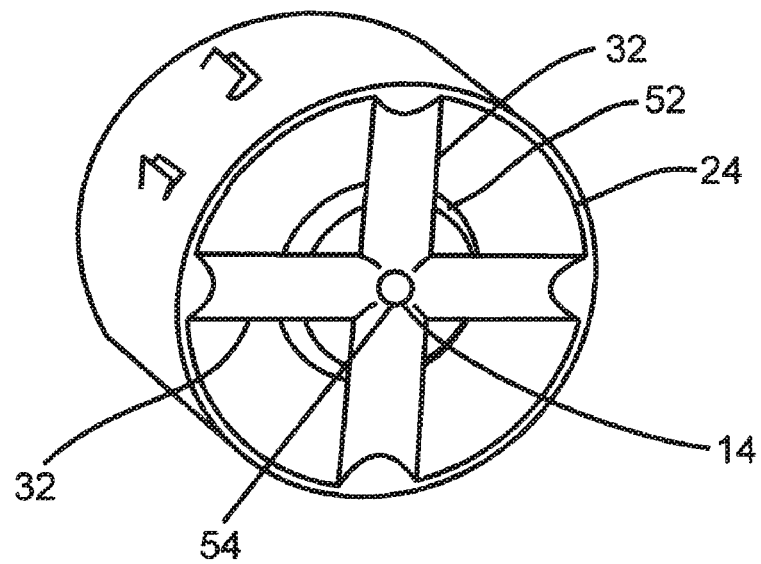
FIG. 9 is a perspective view of a sixth alternate reamer of the system of the invention.

Referring now to FIG. 9, the bar structure 30 is made up of two cross bars 32 which intersect at a center of the cutting form 24. The guide 26 includes an axial hole 54 at the intersection of the bars 32.

Optionally, the cannulation 40 in the holder 34 is sized and surface treated to be a precise, sliding fit with the drill pin 16, in order to provide substantially all axial guidance to the reamer 12 when cutting bone 22.

In another variation, the cannulation 14 in the reamer 12 is a clearance hole.

Alternatively, the cannulation 14 in the reamer 12 is sized and surface treated to be a precise, sliding fit with the drill pin 16, in order to provide substantially all the axial guidance to the reamer when cutting bone 22.

Unlike a traditional reamer (not shown) which cuts a concave form in a bone socket, a profile cutting form 24 cuts a convex form on the external surfaces of bone 22. In other words, the profile cutting reamer cuts a surface which is cylindrical or convex, characterized by having a second derivative which is a positive number, as opposed to a traditional acetabular reamer which cuts a concave form, characterized as having a negative second derivative. Consequently, as mentioned above, the system, designed to cut convex surfaces, is quite different from prior art systems which cut concave surfaces.

In an advantage, the system 10 enables controlled cutting of the femoral joint, while avoiding damage to the femoral stem.

In another advantage, the holder 34 of the invention is easily disassembled for clearning and sterilization.

In another advantage, polished surfaces, particularly in the reamer holder, move heat buildup from the reamer to the holder itself, helping prevent damage to tissue and bone at the operative site.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A reamer system, which comprises:
   a) a reamer, which comprises:
      i) a cylindrically-shaped cutting form having a constant diameter perpendicular to and extending along a longitudinal axis from a proximal cutting form portion to a distal cutting edge;
      ii) an axial guide disposed at least partially inside the cutting form and having a guide length extending from a proximal guide end to a distal guide end; and
      iii) at least two radial bars, each of them having a proximal bar end non-rotatably connected to the axial guide and a distal bar end non-rotatably connected to the cutting form; and
   b) a reamer handle having a bayonet locking device capable of locking the handle to the reamer.

2. The reamer system of claim 1 wherein the axial guide includes a surface offset from a plane of the radial bars at, a distance d.

3. The reamer system of claim 2 wherein the offset surface is preferably polished to reduce friction during relative rotational movement between the offset surface and a second surface referenced to a bone.

4. The reamer system of claim 2 wherein the offset surface is a flange of the axial guide.

5. The reamer system of claim 1 wherein there are three or four bars connecting between the axial guide and the cutting form.

6. The reamer system of claim 1 wherein the bayonet locking device includes recesses which catch portions of the radial bars.

7. The reamer system of claim 1 wherein the reamer comprises a central cannulation that passes from the proximal guide end to and through the distal guide end.

8. The reamer system of claim 7 wherein the cannulation in the guide is a clearance hole.

9. The reamer system of claim 7 wherein the cannulation in the guide is sized and surface treated to be a precise, sliding fit with a drill, pin.

10. The reamer system of claim 1 wherein the reamer handle comprises a corresponding central cannulation that permits a drill pin to pass therethrough.

11. The reamer system of claim 10 wherein the cannulation in the reamer handle is sized and surface treated to be a precise, sliding fit with a drill pin.

12. A reamer, which comprises:
   a) a cylindrically-shaped cutting form having a constant diameter perpendicular to and extending along a longitudinal axis thereof from a proximal cutting form portion to a distal cutting edge;
   b) an axial guide disposed at least partially inside the cutting form and having a guide length extending from a proximal guide end to a distal guide end; and
   c) a bar structure non-rotatably connected to the axial guide at an intermediate bar location between opposed bar ends non-rotatably connected to the cutting form.

13. The reamer of claim 12 wherein an offset surface at the proximal guide end is offset from the bar structure at a distance d.

14. The reamer of claim 12 wherein portions of the bar structure are adapted to releaseably engage a bayonet locking device of a reamer handle.

15. The reamer of claim 12 wherein a central cannulation passes from the proximal guide end to and through the distal guide end.

16. The reamer of claim 15 wherein an axis of the central cannulation of the axial guide defines a common axis with the longitudinal axis of the cutting form.

17. The reamer of claim 12 wherein the bar structure is comprised of a single bar, traversing a center of the cutting form and wherein the axial guide is an axial hole in the bar.

18. The reamer of claim 12 wherein the bar structure is comprised of at least two bars traversing a center of the cutting form and connected to the axial guide which has an axial hole for receiving a drill pin.

19. The reamer of claim 12 wherein the bar structure is comprised of two cross bars which intersect at a center of the cutting form and wherein the axial guide comprises an axial hole at the intersection of the bars.

20. A reamer, which comprises:
   a) a cylindrically-shaped cutting form having a constant diameter perpendicular to and extending along a longitudinal axis from a proximal cutting form portion to a distal cutting edge;
   b) an axial guide disposed at least partially inside the cutting form and having a guide length extending from a proximal guide end to a distal guide end; and
   C) at least two radial bars, each of them having a proximal bar end non-rotatably connected to the axial guide and a distal bar end non-rotatably connected to the cutting form.

21. The reamer of claim 20 wherein a central cannulation passes from the proximal guide end to and through the distal guide end.

22. The reamer of claim 21 wherein an axis of the central cannulation of the axial guide defines a common axis with the longitudinal axis of the cutting form.

23. The reamer of claim 20 wherein the cannulation in the guide is a clearance hole.

24. The reamer of claim 20 wherein the radial bars are adapted to releaseably engage a bayonet locking device of a reamer handle.

25. The reamer of claim 20 wherein the axial guide includes a surface offset from a plane of the radial bars at a distance d.

26. The reamer of claim 25 wherein the offset surface is a flange of the axial guide.

27. The reamer of claim 20 wherein there are three or four bars connecting between the axial guide and the cutting form.

* * * * *